United States Patent
Nulty

(10) Patent No.: US 9,972,989 B2
(45) Date of Patent: May 15, 2018

(54) OPTICAL VOLTAGE SENSING FOR UNDERGROUND MEDIUM VOLTAGE WIRES

(71) Applicant: Aclara Technologies LLC, Hazelwood, MO (US)

(72) Inventor: Gregory M. Nulty, Reston, VA (US)

(73) Assignee: ACLARA TECHNOLOGIES LLC, St. Louis, MO (US)

( * ) Notice: Subject to any disclaimer, the term of this patent is extended or adjusted under 35 U.S.C. 154(b) by 342 days.

(21) Appl. No.: 14/674,079

(22) Filed: Mar. 31, 2015

(65) Prior Publication Data
US 2015/0276818 A1    Oct. 1, 2015

Related U.S. Application Data

(60) Provisional application No. 61/973,007, filed on Mar. 31, 2014.

(51) Int. Cl.
*G01N 21/00*   (2006.01)
*H02G 9/00*    (2006.01)
(Continued)

(52) U.S. Cl.
CPC ............ *H02G 9/00* (2013.01); *G01N 21/553* (2013.01); *G01R 15/16* (2013.01); *G01R 15/242* (2013.01)

(58) Field of Classification Search
CPC .... G01B 7/14; G01M 3/2815; G01M 3/3254; G01M 3/3263; G01M 3/3272
See application file for complete search history.

(56) References Cited

U.S. PATENT DOCUMENTS 3,777,217 A    12/1973   Groce et al.
4,420,752 A    12/1983   Davis et al.
(Continued)

FOREIGN PATENT DOCUMENTS

EP    0 026 801 A1   4/1981
EP    1 505 706 A2   2/2005
(Continued)

OTHER PUBLICATIONS

International Preliminary Report on Patentability and Written Opinion for Application No. PCT/US2012/067285 dated Jun. 12, 2014.
(Continued)

*Primary Examiner* — Michael P Stafira
(74) *Attorney, Agent, or Firm* — Polsinelli PC

(57) ABSTRACT

An optical voltage sensor for measuring voltage on an underground power line or for use in other scenarios in which access to a conductor is available through a blind hole. The optical voltage sensor includes a light modulating member, such as a Pockel's crystal. A reflective, conductive member is positioned at one end of the light modulating member and another conductive member is positioned at an opposed end. A voltage capacitively coupled to the reflective conductive member induces a voltage across the light modulating member, thereby impacting the amount of modulation. A beam of light is directed through the crystal and reflected back out of the crystal, where the amount of modulating can be measured. The amount of modulation indicates a measured voltage, and can be transmitted to a monitoring station where processing can determine the status of the power grid or generate other results based on the measured voltage.

23 Claims, 5 Drawing Sheets

(51) Int. Cl.
*G01N 21/552* (2014.01)
*G01R 15/16* (2006.01)
*G01R 15/24* (2006.01)

(56) References Cited

U.S. PATENT DOCUMENTS

| | | | |
|---|---|---|---|
| 4,581,606 A | 4/1986 | Mallory | |
| 4,689,752 A | 8/1987 | Fernandes et al. | |
| 4,709,339 A | 11/1987 | Fernandes | |
| 4,728,887 A | 3/1988 | Davis | |
| 4,801,937 A | 1/1989 | Fernandes | |
| 4,808,917 A | 2/1989 | Fernandes et al. | |
| 4,829,298 A | 5/1989 | Fernandes | |
| 5,006,846 A | 4/1991 | Granville et al. | |
| 5,235,861 A | 8/1993 | Seppa | |
| 5,426,360 A | 6/1995 | Mario et al. | |
| 5,656,931 A * | 8/1997 | Lau | G01R 19/25 324/522 |
| 5,684,507 A | 11/1997 | Rasnake et al. | |
| 5,684,508 A | 11/1997 | Brilman | |
| 5,684,710 A | 11/1997 | Ehlers et al. | |
| 5,708,679 A | 1/1998 | Fernandes et al. | |
| 5,715,058 A * | 2/1998 | Bohnert | G01R 15/242 324/96 |
| 5,729,144 A | 3/1998 | Cummins | |
| 5,995,911 A | 11/1999 | Hart | |
| 6,005,759 A | 12/1999 | Hart et al. | |
| 6,205,867 B1 | 3/2001 | Hayes et al. | |
| 6,301,514 B1 | 10/2001 | Canada et al. | |
| 6,535,797 B1 | 3/2003 | Bowles et al. | |
| 6,597,180 B1 | 7/2003 | Takaoka et al. | |
| 6,660,934 B1 | 12/2003 | Nourai et al. | |
| 6,751,562 B1 | 6/2004 | Blackett et al. | |
| 6,940,702 B2 | 9/2005 | Kojovic et al. | |
| 7,135,580 B2 | 3/2006 | Bonrath et al. | |
| 7,058,524 B2 | 6/2006 | Hayes et al. | |
| 7,075,308 B2 | 7/2006 | Rockwell | |
| 7,135,850 B2 | 7/2006 | Ramirez | |
| 7,468,661 B2 | 12/2008 | Petite et al. | |
| 7,714,735 B2 | 5/2010 | Rockwell | |
| 7,987,071 B1 | 7/2011 | Dorfman et al. | |
| 8,103,466 B2 | 1/2012 | Taft | |
| 8,536,857 B2 | 9/2013 | Nero, Jr. | |
| 8,587,445 B2 | 11/2013 | Rockwell | |
| 8,896,291 B2 | 11/2014 | Nero, Jr. | |
| 8,941,491 B2 | 1/2015 | Polk et al. | |
| 9,069,009 B2 | 6/2015 | Nero, Jr. | |
| 9,158,036 B2 | 10/2015 | Liu et al. | |
| 2002/0038199 A1 | 3/2002 | Blemel | |
| 2003/0161084 A1 | 8/2003 | Potts et al. | |
| 2003/0216876 A1 | 11/2003 | Premeriani et al. | |
| 2004/0169171 A1 | 9/2004 | Reeves et al. | |
| 2005/0017751 A1 | 1/2005 | Gunn et al. | |
| 2005/0145018 A1 | 7/2005 | Sabata et al. | |
| 2005/0151659 A1 | 7/2005 | Donovan et al. | |
| 2005/0191647 A1 | 9/2005 | Kunsman et al. | |
| 2006/0056370 A1 | 3/2006 | Hancock et al. | |
| 2006/0077918 A1 | 4/2006 | Mao et al. | |
| 2006/0275532 A1 | 12/2006 | Dechert | |
| 2007/0059986 A1 | 3/2007 | Rockwell | |
| 2007/0146147 A1 * | 6/2007 | Kocott | G02B 6/483 340/585 |
| 2008/0036620 A1 | 2/2008 | McCollough | |
| 2009/0027932 A1 | 1/2009 | Haines et al. | |
| 2009/0138229 A1 | 5/2009 | Engelhardt et al. | |
| 2009/0243876 A1 | 10/2009 | Lilien et al. | |
| 2010/0007354 A1 * | 1/2010 | Deaver, Sr. | G01R 31/025 324/539 |
| 2010/0013457 A1 | 1/2010 | Nero, Jr. | |
| 2010/0114392 A1 | 5/2010 | Lancaster | |
| 2010/0152910 A1 | 6/2010 | Taft | |
| 2010/0188239 A1 | 7/2010 | Rockwell | |
| 2010/0237852 A1 | 9/2010 | Tazzari et al. | |
| 2011/0082596 A1 | 4/2011 | Meagher et al. | |
| 2011/0187578 A1 | 8/2011 | Farneth et al. | |
| 2011/0238374 A1 | 9/2011 | Lancaster | |
| 2011/0282508 A1 | 11/2011 | Goutard et al. | |
| 2011/0288777 A1 | 11/2011 | Gupta | |
| 2012/0029871 A1 | 2/2012 | Spillane | |
| 2012/0046799 A1 | 2/2012 | Alex et al. | |
| 2012/0278011 A1 | 11/2012 | Lancaster | |
| 2013/0054162 A1 | 2/2013 | Smith et al. | |
| 2013/0054183 A1 | 2/2013 | Afzal et al. | |
| 2013/0055650 A1 * | 3/2013 | Hartmann | H02G 9/10 52/20 |
| 2013/0076338 A1 * | 3/2013 | Wang | G01R 19/155 324/96 |
| 2013/0134998 A1 | 5/2013 | Kiko et al. | |
| 2013/0205900 A1 | 8/2013 | Nulty | |
| 2013/0328546 A1 | 12/2013 | Nero, Jr. | |
| 2014/0052388 A1 | 2/2014 | Mahlen et al. | |
| 2014/0136140 A1 | 5/2014 | Chan et al. | |
| 2014/0143578 A1 | 5/2014 | Cenizal et al. | |
| 2014/0163884 A1 | 6/2014 | Lilien et al. | |
| 2014/0288863 A1 | 9/2014 | Stevenin | |
| 2015/0069998 A1 | 3/2015 | Nero, Jr. | |
| 2015/0276818 A1 | 10/2015 | Nulty | |
| 2016/0061862 A1 | 3/2016 | Nulty | |

FOREIGN PATENT DOCUMENTS

| | | |
|---|---|---|
| EP | 2 081 273 A2 | 7/2009 |
| GB | 367 244 A | 2/1932 |
| GB | 1 501 351 A | 2/1978 |
| JP | 2004/168914 A | 6/1992 |
| JP | 2006/102308 A | 4/1994 |
| JP | 2010/054863 | 2/1998 |
| WO | WO 99/42844 A1 | 8/1999 |
| WO | WO 00/60367 A1 | 10/2000 |
| WO | WO 01/09628 A1 | 2/2001 |
| WO | WO 2004/068151 A1 | 8/2004 |
| WO | WO 2005/019846 A1 | 3/2005 |
| WO | WO 2005/067686 A2 | 7/2005 |
| WO | WO 2005/091958 A2 | 10/2005 |
| WO | WO 2006/021030 A1 | 3/2006 |
| WO | WO 2006/031739 A2 | 3/2006 |
| WO | WO 2006/092632 A2 | 9/2006 |
| WO | WO 2007/134022 A2 | 11/2007 |
| WO | WO 2009/120537 A1 | 10/2009 |
| WO | WO 2010/127145 A1 | 4/2010 |
| WO | WO 2011/000754 A1 | 1/2011 |
| WO | WO 2013/033387 A1 | 3/2013 |
| WO | WO 2013/076975 A1 | 5/2013 |
| WO | WO 2014/088562 A1 | 6/2014 |
| WO | WO 2014/105018 A2 | 7/2014 |

OTHER PUBLICATIONS

International Preliminary Report on Patentability for Application PCT/US2013/025946 dated Aug. 28, 2014.
International Preliminary Report on Patentability for Application No. PCT/US2012/053106 dated Mar. 13, 2014.
International Preliminary Report on Patentability for Application No. PCT/US2012/053125 dated Mar. 13, 2014.
International Search Report and Written Opinion for Application No. PCT/US2012/053106 dated Jan. 4, 2013.
International Search Report and Written Opinion for Application No. PCT/US2012/053125 dated Jan. 4, 2013.
International Search Report and Written Opinion for Application No. PCT/US2012/067285 dated Mar. 27, 2013.
International Search Report and Written Opinion for Application No. PCT/US2015/023467 dated Oct. 5, 2015.
International Search Report and Written Opinion for Application No. PCT/US2015/047404 dated Dec. 10, 2015.
International Search Report and Written Opinion for International Application No. PCT/US2013/025946, dated May 29, 2013.
ABB Improves Grid Reliability in Algeria, Jun. 13, 2006. http://www.abb.com/cawp/seitp202/d18e8cf73169fbc125714900427925.aspx?
Brambley et al., Wireless Sensor Applications for Buildings Operation and Management. Http://www.buildingsystemsprogram.pnl.gov/wireless/publications/pnnl-sa-43465.pdf. 2005. 40 pages.

(56) References Cited

OTHER PUBLICATIONS

Cooper Power Systems, S.T.A.R. Faulted Circuit Indicators, Bulletin No. 98025, Jun. 1998.
Doig et al., Reclassification of Relay-Class Current Transformers for Revenue Metering Applications, © 2005 IEEE Reprinted from the proceeding of the IEEE T&D PES Conference 1-8.
Govindarasu et al., SST-Sensor Network Design for a Secure National Electric Energy Infrastructure, Iowa State University, Department of Electrical Engineering, 2004. http://www.eng.iastate.edu/abstractsvieewabstract.asp?id=1920.
GridSense website http://www.gridsense.net/products_It30.shtml Aug. 9, 2006.
Hacker et al., Securing America's Power Grid. Iowa State University News Service Relations, 2006. http://www.iastate/edu~nscentral//news/2006/junigrid.shtml.
Nordman et al., Design of a Concept and a Wireless ASIC Sensor for Locating Earth Faults in Unearthed Electrical Distribution Networks, IEEE Transactions on Power Delivery. 2006;21(3):1074-82.
Ozaki et al., A Fault-Tolerant Model for Wireless Sensor-Actor System, IEEE Computer Society, Proceedings of 20th International Conference on Advance Information Networking and Applications. 2006;1-5.
Poisson et al., Detection and measurement of power quality disturbances using wavelet transform. IEEE Transactions of Power Delivery. Jul. 2000;15(3):1039-44.
Risley et al., Electronic Security Risks Associated With Use of Wireless, Point-To-Point Communications in the Electric Power Industry, 2003;1-16.
Santoso et al., Power quality assessment via wavelet transform analysis. IEEE Transaction on Power Delivery. Apr. 1996;11(2):924-30.
Sensors, Controls, and Communications. U.S. Climate Change Technology Program—Technology Options for the Near and Long Term. Aug. 2005;1(3)12-4.
Solodovnik et al., Wireless Sensing and Controls for Survivable AC Zonal System, 2004;1-2. http://www.actapress.com/PaperInfo.aspx?PaperID=17901.
Sun et al., Fault-Tolerant Cluster-Wise Clock Synchronization for Wireless Sensor Networks, IEEE Transactions on Dependable and Secure Computing. 2005;2(3):177-89.
Sushama et al., Detection of power quality disturbances using wavelet transforms. Int J Computer. 2010;18(1):61-6.
U.S. Appl. No. 15/294,545, filed Oct. 14, 2016, Nulty.
U.S. Appl. No. 13/766,524, filed Feb. 13, 2013, Nulty.
U.S. Appl. No. 13/546,577, filed Jul. 11, 2012, Smith et al.
U.S. Appl. No. 13/546,689, filed Jul. 11, 2012, Afzal et al.
U.S. Appl. No. 14/839,570, filed Aug. 28, 2015, Nulty.
U.S. Appl. No. 12/503,417, filed Jul. 15, 2009, Nero.
PCT/US2012/053106, dated Jan. 4, 2013, International Search Report and Written Opinion.
PCT/US2012/053106, dated Mar. 13, 2014, International Preliminary Report on Patentability.
PCT/US2012/053125, dated Aug. 30, 2012, International Search Report and Written Opinion.
PCT/US2012/053125, dated Jan. 4, 2013, International Preliminary Report on patentability.
PCT/US2012/067285, dated Mar. 27, 2013, International Search Report and Written Opinion.
PCT/US2012/067285, dated Jun. 12, 2014, International Preliminary Report on patentability.
PCT/US2013/025946, dated May 29, 2013, International Search Report and Written Opinion.
PCT/US2013/025946, dated Aug. 28, 2014, International Preliminary Report on Patentability.
PCT/US2015/023467, dated Oct. 5, 2015, International Search Report and Written Opinion.
PCT/US2015/047404, dated Dec. 10, 2015, International Search Report and Written Opinion.

* cited by examiner

OPTICAL VOLTAGE SENSING FOR UNDERGROUND MEDIUM VOLTAGE WIRES

RELATED APPLICATIONS

The present application claims priority under 35 U.S.C. § 119(e) to U.S. Provisional Application Ser. No. 61/973,007, entitled "OPTICAL VOLTAGE SENSING FOR UNDERGROUND MEDIUM VOLTAGE WIRES" filed Mar. 31, 2014, which is incorporated herein by reference in its entirety.

BACKGROUND OF INVENTION

Power lines form an important part of the power distribution system, carrying power from generation facilities all the way to the locations where it is used. The power distribution system may include many types of power lines, with high voltage lines used closer to the power generation facilities and medium and lower voltage lines closer to the locations where the power is used. These lines may run overhead. Alternatively power lines, particularly medium voltage lines, may run underground. Many commercial buildings, for example, receive power through underground power lines.

A power company may desire to obtain accurate voltage measurements of power lines in its power distribution system. Measurements may be used for multiple purposes, such as to detect or predict faults in the lines or to manage the power distribution system. For example, voltage measurements may be used to manage voltage levels and the amount of reactive power throughout the power distribution system (e.g., by using the measured voltage to determine how to operate switched capacitor banks and/or other components of a power distribution system). As another example, voltage measurements may be used to detect power theft.

Measuring voltage on underground wires poses special difficulties. Though underground wires are generally used for medium voltage, they might nonetheless carry tens of thousands of volts. For safety reasons, these lines are heavily insulated to prevent humans from accidentally contacting conductors at that voltage. Conventional approaches to measuring the voltage of underground power lines involve a voltage test port that enables access to the line through the insulation. Such a test port may be built into the cable connectors, elbows, or splices and allows a probe to be brought near enough the power line for a voltage to be capacitively coupled to the probe. The probe can then measure the capacitively coupled voltage, which indicates the voltage on the power line.

BRIEF SUMMARY OF INVENTION

Improved power line voltage sensing may be facilitated with sensors placed at key locations in a power distribution system, including underground locations. The sensors may be used in a system that provides above-ground access to underground voltage measurements. In some embodiments, sensors may be embedded into components connected together in installing the underground power line. Voltage measurements may be used in any suitable way. For example, data from multiple underground and/or above ground sensors may be aggregated and analyzed to determine the presence or magnitude of voltage on the power line. This information may be used to determine the performance of the power distribution system, detect or predict faults and/or to promote safe access to the power line.

A system for sensing voltage on an underground power line may include a sensor unit embedded into components that might otherwise be present in the power line. The sensor unit may operate by modulating light in a way that indicates voltage on the line. The sensor may be configured for easy incorporation into an underground power distribution system and may allow measurements through an opening in an insulative covering on a power line. The sensor may be sized to fit within a test port or other opening in the insulation on a medium voltage underground line. A power source, a light source, and a detector may also be incorporated into the sensor unit to make a self-contained unit, such that multiple sensor units may be distributed throughout a power distribution system.

According to an aspect of the present application an optical voltage sensor is provided. The optical voltage sensor comprises a light modulating member comprising a first end and a second end. The light modulating member changing a property of light passing through the member based on a voltage on the light modulating member. The optical voltage sensor further comprises a conductive, reflective member disposed at the first end and a conductive member disposed at the second end of the light modulating member.

In some embodiments, the light modulating member comprises a phase-changing material. In some embodiments, the conductive member at the second end comprises an opening therethrough. The opening being positioned such that a beam of light passing into the light modulating member through the opening is reflected from the conductive, reflective member. In some embodiments, the light modulating member comprises a crystal exhibiting the Pockel's effect. In some embodiments, the conductive, reflective member comprises a layer of reflective material and a layer of conductive material. In some embodiments, the optical voltage sensor further comprises a laser configured to direct a beam of light through the light modulating member towards the conductive, reflective member, and a detector configured to receive the beam of light reflected from the conductive, reflective member and to determine an amount of modulation introduced on the light beam within the light modulating member. In some embodiments, the optical voltage sensor further comprises a transmitter configured to transmit a signal indicative of the amount of modulation.

According to an aspect of the present application a method of measuring voltage on an underground power line is provided. The method comprises directing a beam of light through a light modulating member positioned with a voltage of the underground power line coupled to the light modulating member. The light modulating member changing a property of light passing through the member based on the voltage. The method further comprises reflecting the beam of light, receiving the reflected beam of light, and determining an amount of modulation on the beam of light introduced within the light modulating member.

In some embodiments, the light modulating member comprises a crystal exhibiting the Pockel's effect. In some embodiments, determining an amount of modulation comprises measuring a phase change between the beam of light as incident on the light modulating member and the reflect beam of light after exiting the light modulating member. In some embodiments, the method further comprises transmitting an indication of the determined amount of modulation. In some embodiments, the method further comprises receiving the indication of the determined amount of modulation at a processor and determining with the processor, based on the indication, a status of a power grid comprising the power line. In some embodiments, determining the status comprises determining the voltage on the power line. In some embodiments, determining the status comprises detecting a fault or power quality within the power grid. In some embodiments, directing the beam of light through the light modulating member comprises directing the beam through an opening in a conductive layer on a surface of light modulating member.

According to an aspect of the present application a system is provided. The system comprises an underground power line comprising a capacitive test access port and an optical voltage sensor disposed at least partially disposed within the test access port.

In some embodiments, the optical voltage sensor comprises a light modulating member comprising a first end and a second end, the light modulating member changing a property of light passing through the member based on a voltage on the light modulating member. In some embodiments, the optical voltage sensor further comprises a conductive, reflective member disposed at the first end, and the first end is disposed within the test access port with the conductive, reflective member coupled to a conductor of the power line. In some embodiments, the optical voltage sensor further comprises a battery and an inductive power pickup configured to couple power from the power line to charge the battery. In some embodiments, the power line comprises a multi-phase power line having a plurality of phases and the system further comprises a plurality of optical voltage sensors, the optical voltage sensor being one of the plurality of optical voltage sensors. Each of the plurality of optical voltage sensors is capacitively coupled to a phase of the plurality of phases. The system further comprises a laser and a splitter adapted to direct a portion of a beam from the laser to each of the plurality of optical voltage sensors.

According to an aspect of the present application a system is provided. The system comprises an underground power line comprising a capacitive test access port and a sensor system at least partially disposed within the test access port. In some embodiments, the sensor system includes a voltage sensor. In some embodiments, the sensor system includes a current sensor. In some embodiments, the system includes a processor that processes voltage and current measurements. In some embodiments, the system includes a current sensor. In some embodiments, the system includes a processor that processes voltage and current measurements. In some embodiments, the system includes an automatic data analysis system.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, no every component may be labeled in every drawing. In the drawings.

DETAILED DESCRIPTION OF INVENTION

Figure 1:
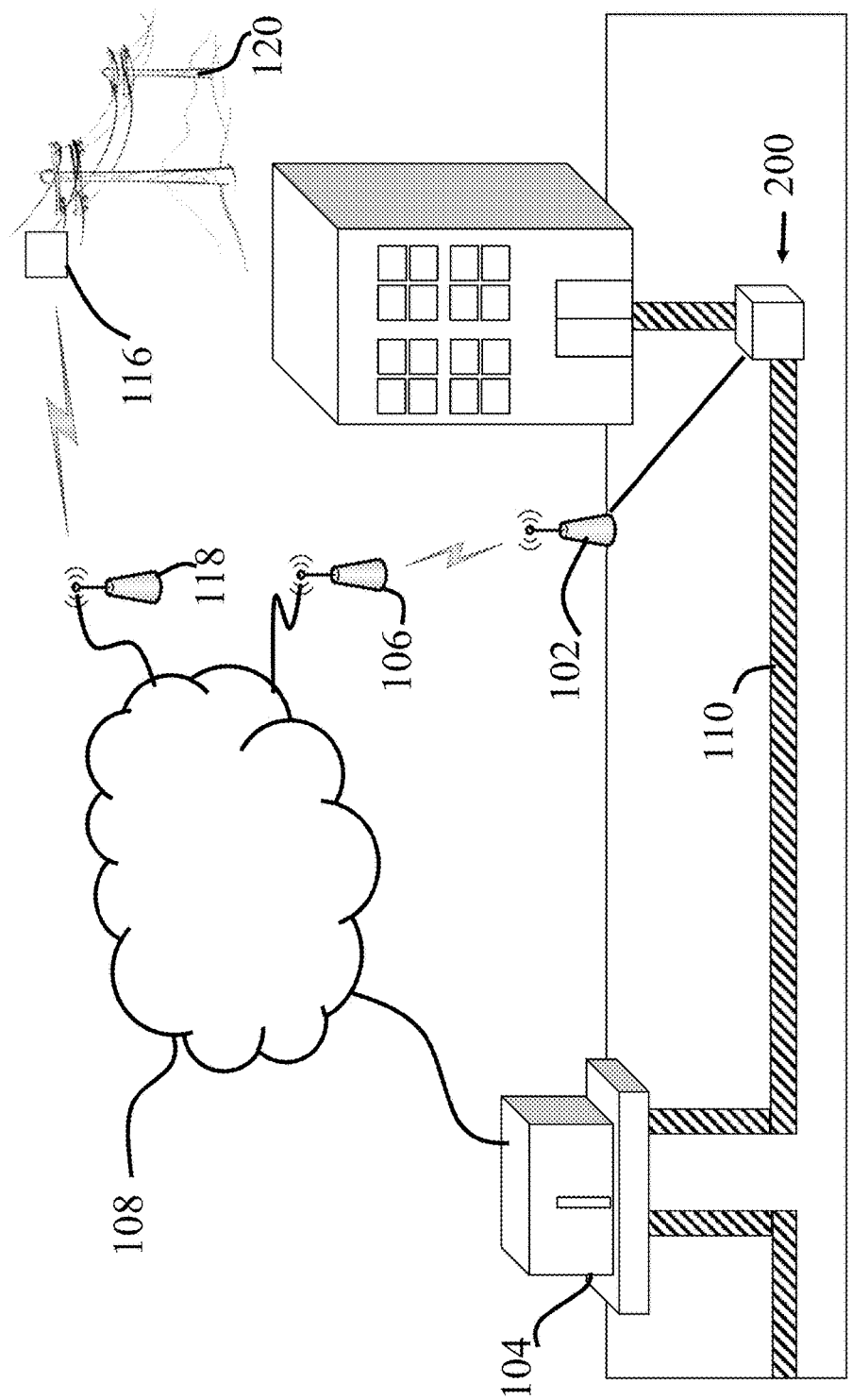
FIG. 1 is a schematic illustration of an underground power distribution system equipped with components for sensing and taking measurements of the voltage on an underground power line.

The inventor has recognized and appreciated that improved management and maintenance in a power distributions system may be achieved with an improved sensor, configured to measure voltage of underground power lines. The sensor may be an optical sensor and may be configured for operation within a test access location in a power line. The sensor may be implemented in any suitable way, including with a Pockel's effect optical crystal. Such a system may more easily, accurately and safely measure the voltage of an underground medium voltage power line.

An optical sensor may be constructed using a material that alters a measurable parameter of light based on a voltage applied to the material. Such an optically modulating material, for example, may modulate amplitude or phase of a beam of light passing through the material in an amount related to a voltage applied to the material. A Pockel's crystal is used herein as an example of a phase-changing material. As is known in the art, a Pockel's crystal will change the phase of light passing through the crystal. The amount of phase change is related to the voltage across the crystal. Thus, measuring phase change of a light beam passing through the crystal, provides an indication of the voltage applied to the crystal. Examples of Pockel's crystals are those containing ammonium dihydrogen phosphate, potassium dihydrogen phosphate, potassium dideutrim phosphate, potassium dihydrogen arsenate, rubidium dihydrogen phosphate, and ammonium dihydrogen arsenate. However, any material or combination of materials exhibiting suitable light modulation properties alternatively or additionally may be used.

By positioning the crystal so that the voltage across the crystal is derived from the voltage on the power line to be measured, the phase change of the crystal indicates the voltage on the power line. In some embodiments, the crystal is capacitively coupled to the power line and may be placed near the power line, such as within the test port or other opening in the insulation of an underground line.

The inventor has recognized and appreciated a sensor configuration that allows an optical measurement to be made on a line that has an insulative covering or to which physical access is otherwise restricted. The crystal material may be combined with a light reflective material, at a first end of the phase changing material. During operation, a light beam may be injected from a second end of the crystal and directed towards the reflective material at the first end. The light beam may be reflected to another location where it can be accessed for measurement. As a result, a measurement can be made on light passing through the crystal, even if portions of the crystal cannot be readily accessed.

Such a configuration enables a sensor to be inserted into a test port of a medium voltage underground wire or other similar configuration in which access is constrained. The first end, with the reflective material, may be placed within the test port. A laser beam may be both injected into the crystal and measured after passing through the crystal from outside the test port.

To facilitate coupling of a power line voltage across the crystal, the reflective material may also be conductive or may be formed with a conductive material. A conductive material, positioned near a power line, may result in a voltage on the power line being capacitively coupled to the conductive material. The amount of voltage coupled from the line to the conductive material may depend on the physical configuration of the sensor and its proximity to a conductor of the power line. The ratio of voltage on the line to voltage coupled to the sensor may be determined through computation or measured as part of a calibration process. As a result, a measurement of the voltage coupled to the sensor may be related to the voltage on the power line.

Any suitable conductive material may be placed on or near the crystal. An example of a suitable material is silver, which is both reflective and conductive. In other embodiments, gold or other metals or metal alloys may be used. However, it should be appreciated that it is not a requirement that a single material be used to form a reflective, conductive member. Such a member may be formed using both a reflective and a conductive material. These different materials may be formed as layers that are integrally formed into a member, such as by brazing or depositing a reflective coating on a conductive layer. In other embodiments, the reflective and conductive layers need not be integral and may simply be positioned close enough to the crystal to reflect light passing through it or to couple a voltage from the power line.

This conductive material may be placed near the line on which a measurement is being made such that voltage on the line will couple to the sensor. For example, the sensor may be configured such that the reflective material is at the bottom of the test port, adjacent the line being measured.

A second conductive member may also be applied at a second end of the crystal. By coupling the second conductive member to ground, or other suitable reference potential, a voltage will be established across the crystal. A beam of light passing through the light may be modulated in proportion to the magnitude of that voltage. Because the voltage across the crystal may be correlated to the voltage across, a measurement of modulation introduced on the light beam may indicate the voltage on the line. In the case of a phase-changing crystal, the modulation may be in the form of a phase change such that a measured phase differential between an input beam and an output beam may be related to voltage on the line.

The light source may be a coherent light source, such as a laser. A coherent light source may facilitate measurements of a change of phase. When the optically modulating material in the sensor impacts another property of light, such as its amplitude, a non-coherent source may alternatively or additionally be used, such that the specific light source used.

In some embodiments, mirrors and/or lenses may be placed between the source and the Pockel's crystal and/or between the Pockel's crystal and the detector. These mirrors may act as optical guides that direct a light beam into and out of the Pockel's crystal. Such mirrors may provide flexibility in the physical orientation of the light source and detector with respect to the crystal.

Sensors as described above may be deployed to measure voltage on a poly-phase line. In some embodiments, a sensor may be attached to a conductor associated with each phase. In some embodiments, multiple sensor units may share a light source and/or a detector. For example, power lines may be poly-phase, such that a power line may contain multiple conductors on which voltage measurements are to be made. In the example of a three phase distribution line, measurements may be made on all three conductors at the same location. Separate sensor units may be coupled to each conductor. A single light source, such as a laser, may be passed through a splitter to generate multiple beams, each directed at one sensor unit. The light exiting from each sensor unit may be routed to a detector. The light from the sensors may be routed to separate detectors or may be routed through an optical combiner, and then directed to a single sensor. In embodiments in which a single detector is used, an optical multiplexor or optical switches may be included in the path between the source and detectors so that light from the source passing thorough only a single sensor at a time reaches the detector. Accordingly, the specific configuration of the optical path between a light source and a detector is not critical to the implementation of a sensor system.

To facilitate use in a distributed sensor system, the sensor may derive power from the power line. Power may be inductively coupled from the line. However, other power sources, such as batteries, fuel cells or super capacitors may be employed.

Other measurement circuitry may alternatively or additionally be included within the sensor unit. Current measurement circuitry may be included. Such circuitry may operate with a Hall-effect sensor, Rogowski coil, current transformer, or measure current in any other suitable way. Alternatively or additionally, environmental sensors may be included in the sensor unit. For example, temperature or moisture sensors may be included.

Further, the sensor unit may include circuitry to facilitate communication of measurements to a remote processing site. Communication circuitry may alternatively or additionally receive commands that configure the sensor unit, cause the sensor unit to take measurements, or otherwise control the sensor unit. Such communication circuitry may operate wirelessly or may communicate over the power line or via another line.

An optical sensor as described herein may be part of a distributed sensor system, with sensors at multiple locations in the power grid. Voltage measurements made with such sensors may be used to monitor the performance of the power line or determine the safety status of the power line. This data may further facilitate maintenance of inaccessible physical cables and avoidance of unsafe conditions (such as contacting a power line that is still live following a power outage).

The following figures provide examples of possible embodiments of sensors and systems employing such sensors. The embodiments illustrated in the figures are exemplary and not limiting of the invention.

FIG. 1 illustrates an environment in which the techniques described herein for sensing and measuring a voltage on an underground power line may be applied. Here, an underground, medium voltage power distribution line 110 is illustrated. Physical access to line 110 is restricted by earth and buildings. Coupled to the power distribution line is a sensor system 200. Sensor system 200 may include optically modulating material positioned to respond to voltage on the line, optics and circuitry to take measurements, including current measurements from the line. Though not specifically shown in FIG. 1, such circuitry may include a processor that executes control algorithms or responds to commands to collect and process data from a sensor.

Sensor system 200 may include circuitry to facilitate communication of measurements to a remote processing site and to facilitate receipt of commands. In the embodiment illustrated, sensor system 200 is associated with an RF transceiver 102. That transceiver may be physically integrated into a housing containing measurement circuitry. However, the transceiver may be located in a separate housing, coupled via a cable, such as a coaxial cable, or other suitable element to the components that acquire measurements. In embodiments in which the sensor system is underground, the associated transceiver may be located above ground or in any suitable location.

The remote location with which the sensor system communicates is not critical to the invention. However, in some embodiments, a utility company may operate a control center 104. The control center 104 may receive and process measurements received from sensors in the power distribution network. Those sensors may include sensors associated with sensor system 200, providing measurements for an underground line. Alternatively or additionally, those measurements may be obtained from above ground lines, such as from sensor system 116 attached to an above ground line.

In some embodiments, the sensor systems, because they are distributed throughout the power distribution system may communicate to control center 104 totally or partially wirelessly. In the embodiment illustrated, transceivers are coupled to a wired network 108 and distributed over the geographic area where sensor systems are located. Transceivers, such as transceiver 106 and transceiver 118 may receive data from and send commands to transceivers, such as transceiver 102 wired to sensor system 200 or a transceiver (not shown) associated with sensor system 116.

Any or all of these components may communicate wireless. However, any or all of these components might be coupled together through network 108, which may be a public network, such as the internet, or a private network, such as might be maintained by a power distribution company for digital communication of status and control information. Network 108 alternatively may be implemented using a cellular network in whole or in part.

The control center 104 may issue commands to the sensor systems to trigger measurements or reporting of measurements. The functions of the control center may be implemented in one or more computer processors programmed to execute data analysis and control algorithms. Such algorithms, for example, may control the collection of data from one or multiple sensors throughout a power distribution network. Such algorithms may also process the measurements to detect faults, predict performance problems, indicate an upcoming need for maintenance, or perform any other suitable processing.

Sensor systems can be attached to the power distribution line at any one or multiple locations along the line. In some embodiments, sensor systems may be selectively placed in the power distribution system such as in existing components. For example, sensors may be integrated into cable connectors, elbows, or splices. Such components may be designed with test access ports and the sensor systems may be shaped to fit at least partially within the test access port. However, sensors may be mounted in any suitable locations. Thus, it should be appreciated that the number and location of the sensor systems is not critical to the invention.

It also should be appreciated that FIG. 1 shows a simplified representation of a power distribution system. A power distribution system may have many more underground and overhead power lines than illustrated. Thus, it should be appreciated that the specific type and structure of the lines to which sensor units are attached is not critical to the invention. Sensor systems may be attached to any suitable type of line, including cables of various types.

Figure 2:
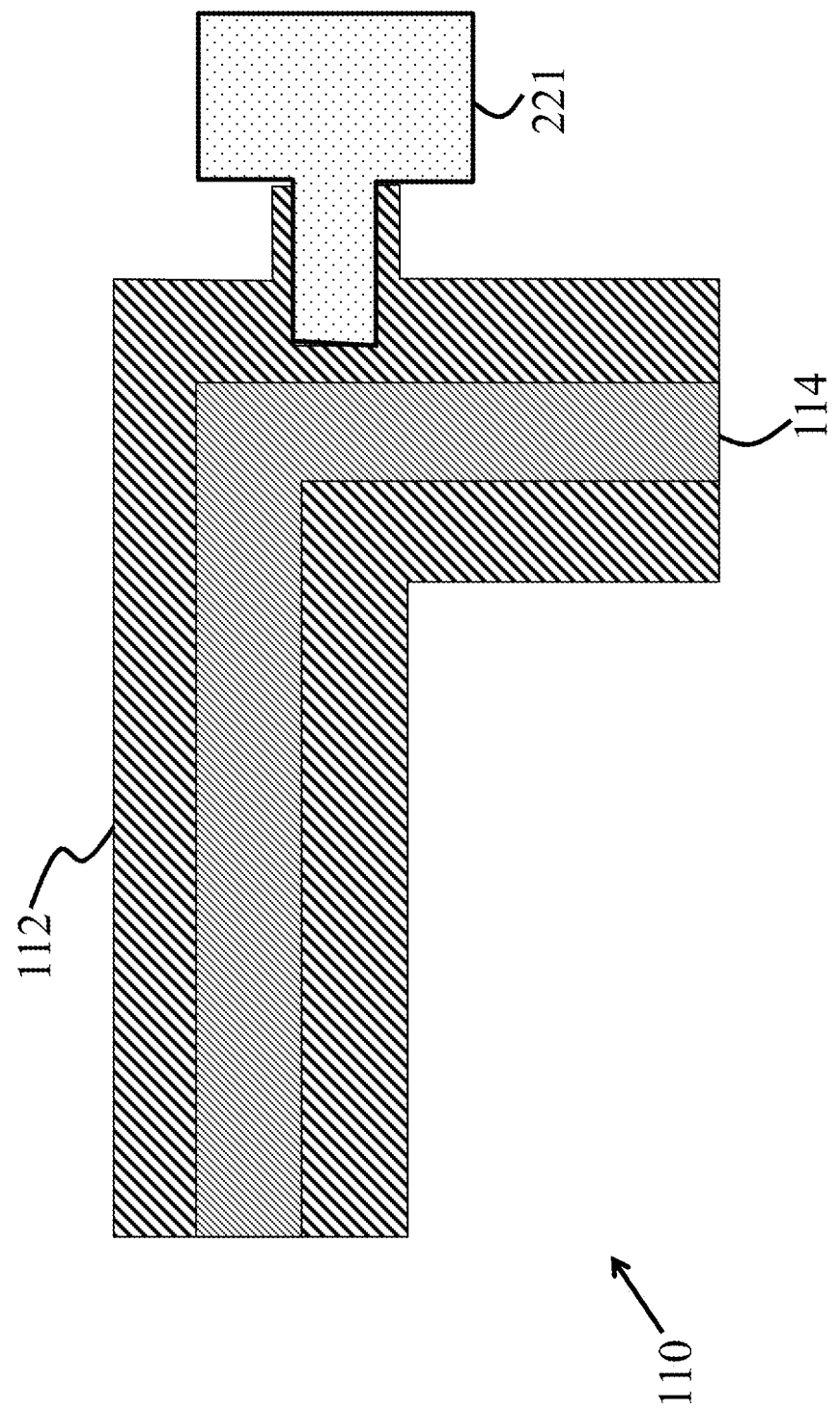
FIG. 2 is a schematic illustration of a test access port in accordance with some embodiments of a system for sensing and measuring the voltage on an underground power line.

FIG. 2 illustrates an embodiment of power line 110 to which sensor system 200 is attached. In this example, the portion illustrated includes an elbow, which may be implemented using components as are known in the art. In this example, the elbow includes a test access port. Sensor probe 221 is configured for easy incorporation into an underground power distribution system. In this example, sensor probe 221 is sized to fit at least partially within a test access port on the medium voltage underground line. Sensor probe 221 measures voltage on conductor 114. Here, sensor probe 221 is inserted in an opening in an insulative covering 112 on the power line. In this example, that opening may be a test access port. As shown, sensor probe 221 at least partially fits within the test access port. The portion within the test access port may include a crystal and a reflector. Other components of the sensor, such as a light source, detector and processing circuitry may be located outside of the test access port.

Figure 3:
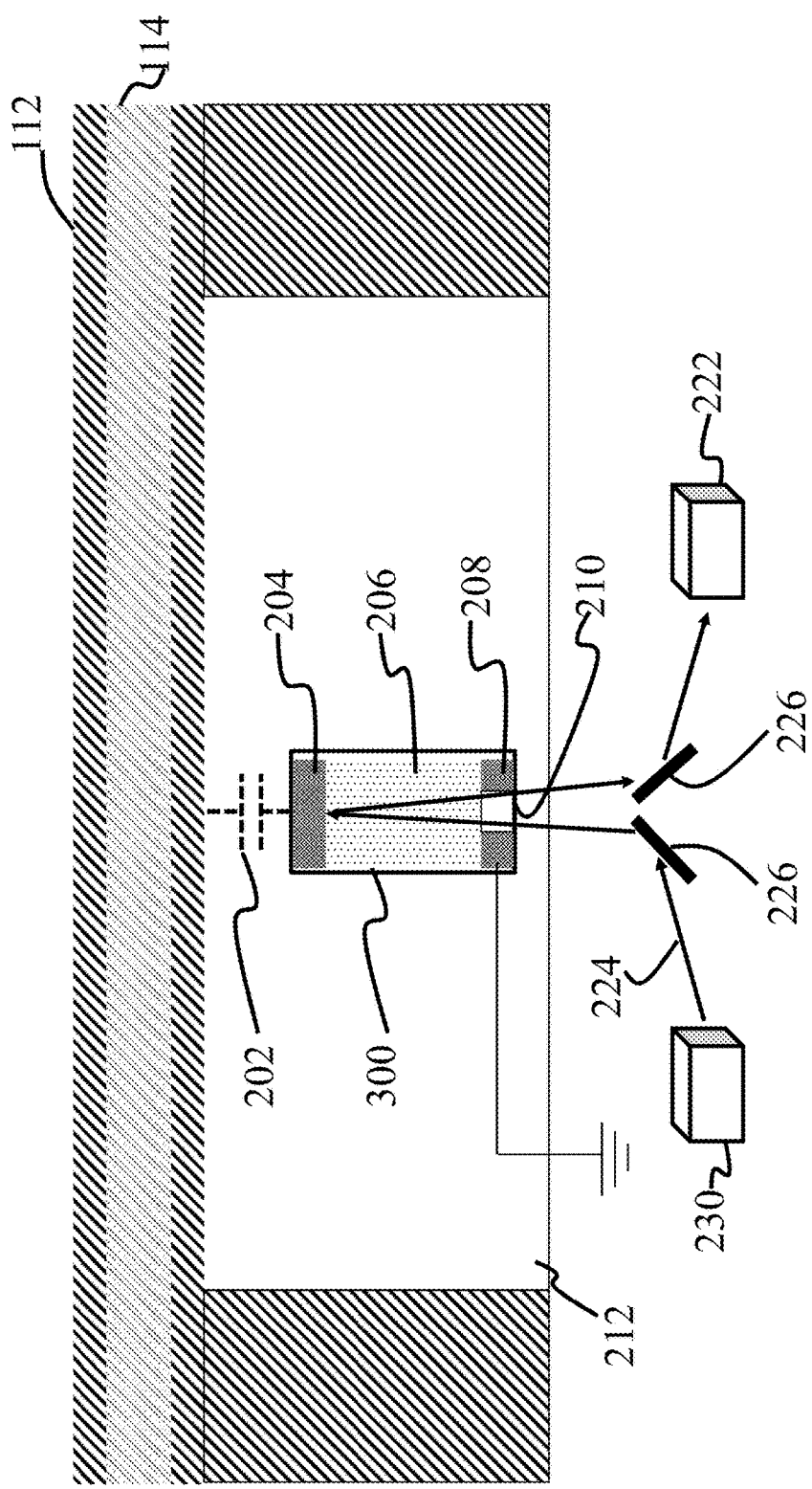
FIG. 3 is a schematic illustration of a sensor configuration in accordance with some embodiments of a system for sensing and measuring the voltage on an underground power line.

FIG. 3 schematically illustrates an embodiment in which sensor probe 221 is installed, at least partially, in a test access port 212. In this example, the test access port 212 may have a diameter of approximately 0.5 inches wide and 2 inches deep. In this example, a Pockel's crystal 206 is capacitively coupled, as illustrated by symbol 202, to the conductor 114 through the insulative covering 112. Here, that capacitive coupling is to a reflective conductive member 204. A second conductive member 208, at an opposite end of crystal 206, is grounded, forming a voltage differential such that a voltage will be induced across the crystal that is related to the voltage on conductor 114. The crystal will change the phase of light in relation to the voltage across the crystal. Sensor detector 222 measures the phase change on the laser beam 224 as it passes through the Pockel's effect optical crystal 206.

In the embodiment illustrated, reflective components are used to route light into and out of the crystal. Here, a laser emitter 220 emits a single laser beam 224 onto a polarizer 226. Polarizer 226 directs the laser beam through an opening 210 in the conductive member 208. The conductive member 208 acts as an electrode. For example, it may be a conductive member made of silver coupled to ground to act as a reference voltage for the Pockel's crystal 206.

Laser beam 224 passes through opening 210 and into the Pockel's effect optical crystal 206 towards a reflective member 204. Reflective member 204 may be made of silver and is placed at the top of the Pockel's crystal 206. The crystal 206 with the reflective member 204 is oriented such that the reflective member is at the bottom of the test port, adjacent the line 110 being measured.

Laser beam 224 is then reflected off the reflective member 204 and back down through the Pockel's crystal 206.

If a voltage is present on conductor 114, then that voltage will be capacitively coupled, as illustrated by symbol 202. This voltage is applied across the Pockel's crystal 206. This applied voltage causes the phase-modulating crystal 206 to change the phase of laser beam 224 in an amount related to a voltage applied across crystal 206.

Laser beam 224 then leaves the Pockel's crystal 206 through the opening 210 and reaches a polarizer 226. Polarizer 226 directs beam 224 into a light detector 222. Light detector 222 may determine the relative phase on the light beam 224 at the source 220 relative to when it has reached detector 222. The phase change represents a voltage measurement.

In the embodiment illustrated, some of the components of a sensor probe 221 are shown within test access port 212. It should be appreciated that only portions of the sensor may be positioned within the test access port. For example, crystal 206, with attached conductive members acting as electrodes may be within the test access port, but laser source 220 and detector 222, along with polarizer 226 and other circuitry may be outside of the test access port. However, the specific arrangement of the components is not critical to the invention.

Figure 4:
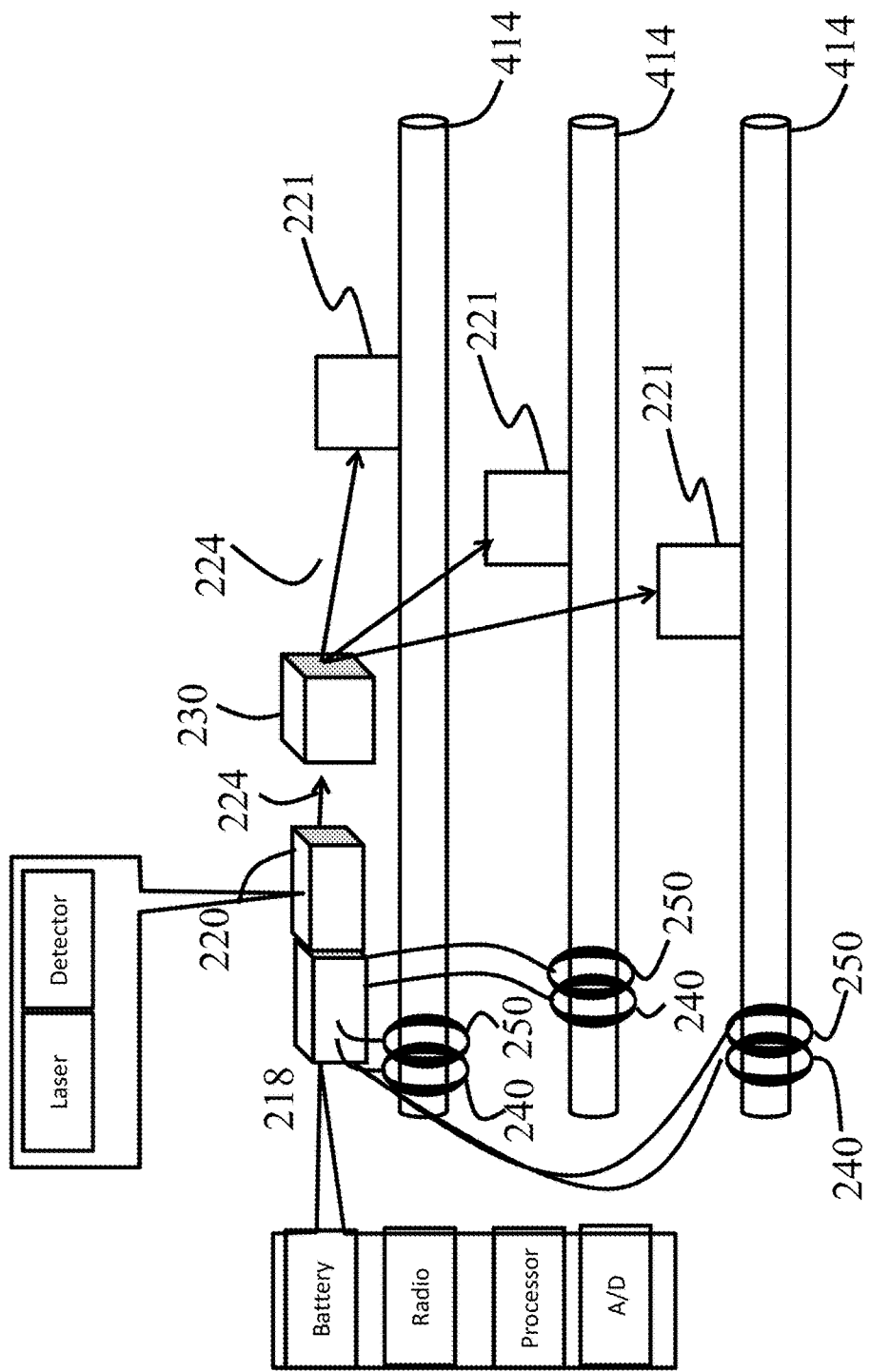
FIG. 4 is a schematic illustration of a system with an input light source splitter in accordance with some embodiments for sensing and measuring the voltage on a three-phase power line.

FIG. 3 illustrates a single sensor attached to a single conductor. In other embodiments, multiple sensors may be attached to a power line at one location. FIG. 4 illustrates an example of multiple sensor systems sharing a light source and/or a detector. Here, a three-phase power line, made of three voltage-carrying conductors 414, is illustrated. One sensor probe 221 is coupled to each conductor 414. These three sensor probes 221 share a single light source 224. A single laser beam 224 is emitted from emitter 220. Beam 224 passes through a beam splitter 230 that generates three separate beams 224, each directed at one sensor probes 221. Each sensor probe 221 then takes a voltage measurement for an associated conductor 414 in the manner described in FIG. 3. In this example, a voltage measurement is made on all three conductors 414 at the same location.

In other embodiments, each phase in the three-phase power line may have its own laser light source, which may be packaged as a unit with corresponding components, such as is illustrated by laser unit 220. Control unit 218 may comprise a collection of parts for detection, processing commands and/or data, communicating commands and/or data and supplying power to sensor system 200. Control unit 218 may include a battery, radio, processor, and an analog to digital converter. In some embodiments, the processor in laser unit 220 may perform an automatic data analysis of data received from sensor probe 2021. Control unit 220 may be packaged as a kit in connection with one or more sensor units adapted for installation at a particular location in a power distribution network.

For example, each line in the 3-phase power line of FIG. 4 may include two coils. One coil may be used to sense current on each phase. In some embodiments, this coil may be a Rogowski coil 240. The second coil 250 may be used to inductively supply power to sensor system 200. The coils may be packaged as part of a kit, but may be supplied in any suitable way.

Figure 5:
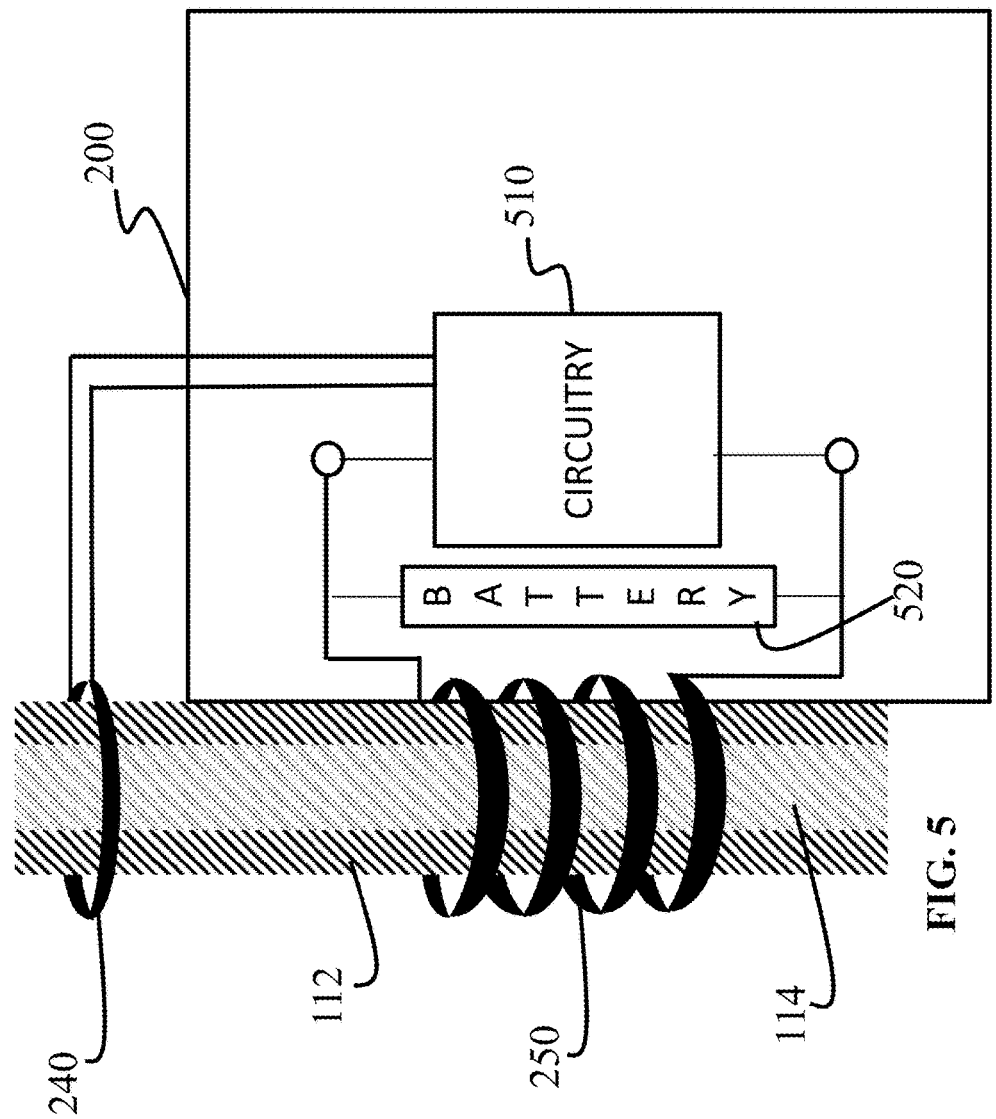
FIG. 5 is a schematic illustration of an inductive power source in accordance with some embodiments of a system for sensing and measuring the voltage on an power line.

FIG. 5 illustrates a power source configuration for sensor system 200. To facilitate use in a distributed sensor system, the sensor system 200 may derive power from the power line. In this example, power is inductively coupled from the conductor 114 using a coil 250. Power coupled using coil 250 may charge a battery 520. In other embodiments, that power may be derived from a battery or any other suitable source. That power may be coupled to circuitry 510 and other active components. Circuitry 510 may include a coherent light source and/or a detector. Alternatively or additionally, circuitry 510 may include a processor, which may be programmed to execute control and/or signal processing algorithms. Circuitry 510 also may include a transceiver and/or other suitable communication circuitry.

Having thus described several embodiments, it is to be appreciated various alterations, modifications, and improvements may readily occur to those skilled in the art. Such alterations, modifications, and improvements are intended to be within the spirit and scope of the invention. Accordingly, the foregoing description and drawings are by way of example only.

Various changes may be made to the illustrative structures shown and described herein. For example, embodiments were described in which an optical voltage sensor is configured for measuring a voltage on an underground medium voltage line. However, the techniques as described herein may be applied in sensors suitable for other uses. A sensor may be configured to measure a voltage of lower or higher voltage lines. Alternatively or additionally, the sensor may be configured for above ground power lines. Further, it is not a limitation that the sensor be used to measure voltage on power lines. An optical voltage sensor constructed with the techniques described herein may be used to measure voltage of any conductor, and may be particularly useful in scenarios in which access to the conductor is through a blind hole in an insulative structure.

As another example, a sensor is described as attached to a power line. It is not a requirement that the sensor be permanently attached to the line or even be attached at all. A sensor as described herein, for example, may be embodied in a hand-held unit that acts as a probe. The probe may have a tip sized and configured for insertion into a test access port. The handheld unit may have any suitable output mechanism to indicate a voltage measured with the sensor.

As another example, control and data analysis functions were described. Such functions can be implemented in any of numerous ways. For example, the embodiments may be implemented using hardware, software or a combination thereof. When implemented in software, the software code can be executed on any suitable processor or collection of processors, whether provided in a single computer or distributed among multiple computers. Such processors may be implemented as integrated circuits, with one or more processors in an integrated circuit component. Alternately, a processor may be implemented using circuitry in any suitable format.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone, a tablet, or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, touch screens, and digitizing tablets. As another example, a computer may receive input information through speech recognition or in other audible format.

Such computers may be interconnected by one or more networks in any suitable form, including as a local area network or a wide area network, such as an enterprise network or the Internet. Such networks may be based on any suitable technology and may operate according to any suitable protocol and may include wireless networks, wired networks or fiber optic networks.

Also, the various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, the invention may be embodied as a computer readable storage medium (or multiple computer readable media) (e.g., a computer memory, one or more floppy discs, compact discs (CD), optical discs, digital video disks (DVD), magnetic tapes, flash memories, circuit configurations in Field Programmable Gate Arrays or other semiconductor devices, or other tangible computer storage medium) encoded with one or more programs that, when executed on one or more computers or other processors, perform methods that implement the various embodiments of the invention discussed above. As is apparent from the foregoing examples, a computer readable storage medium may retain information for a sufficient time to provide computer-executable instructions in a non-transitory form. Such a computer readable storage medium or media can be transportable, such that the program or programs stored thereon can be loaded onto one or more different computers or other processors to implement various aspects of the present invention as discussed above. As used herein, the term "computer-readable storage medium" encompasses only a computer-readable medium that can be considered to be a manufacture (i.e., article of manufacture) or a machine. Alternatively or additionally, the invention may be embodied as a computer readable medium other than a computer-readable storage medium, such as a propagating signal.

The terms "program" or "software" are used herein in a generic sense to refer to any type of computer code or set of computer-executable instructions that can be employed to program a computer or other processor to implement various aspects of the present invention as discussed above. Additionally, it should be appreciated that according to one aspect of this embodiment, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags or other mechanisms that establish relationship between data elements.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, the invention may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Also, circuits and modules depicted and described may be reordered in any order, and signals may be provided to enable reordering accordingly.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

What is claimed is:

1. An optical voltage sensor system, comprising:
   a splitter adapted to output multiple beams from a light received from a light source;
   a plurality of optical voltage sensors; each sensor receiving a beam of light from the splitter and comprising:
      a light modulating member comprising a first end and a second end, the light modulating member changing a property of light passing through the member based on a voltage on the light modulating member, wherein the voltage is generated by an external voltage source having a plurality of phases, and wherein the sensor is capacitively coupled to a phase of the plurality of phases;
      a conductive, reflective member disposed at the first end; and
      a conductive member disposed at the second end of the light modulating member, wherein the light enters and exits the second end of the light modulating member.

2. The optical voltage sensor system of claim 1, wherein for each sensor:
   the light modulating member comprises a phase-changing material.

3. The optical voltage sensor system of claim 1, wherein for each sensor:
   the conductive member at the second end comprises an opening therethrough, the opening being positioned such that a beam of light passing into the light modulating member through the opening is reflected from the conductive, reflective member.

4. The optical voltage sensor system of claim 1, wherein for each sensor:
   the light modulating member comprises a crystal exhibiting the Pockel's effect.

5. The optical voltage sensor system of claim 1, wherein for each sensor:
   the conductive, reflective member comprises a layer of reflective material and a layer of conductive material.

6. The optical voltage sensor system of claim 1, further comprising:
a transmitter configured to transmit a signal indicative of the amount of modulation.

7. A method of measuring voltage on a multiphase underground power line, the method comprising:
directing a beam of light through a splitter adapted to output multiple beams from a light received from a light source;
directing a particular beam of the multiple beams through a light modulating member of an optical sensor, positioned to detect a phase of the multiphase underground power line coupled to the light modulating member, the light modulating member changing a property of light for the particular beam passing through the member based on the voltage;
reflecting the particular beam of light;
receiving the reflected particular beam of light; and
determining an amount of modulation on the particular beam of light introduced within the light modulating member.

8. The method of claim 7, wherein:
the light modulating member comprises a crystal exhibiting the Pockel's effect.

9. The method of claim 8, wherein:
determining an amount of modulation comprises measuring a phase change between the beam of light as incident on the light modulating member and the reflect beam of light after exiting the light modulating member.

10. The method of claim 7, further comprising:
transmitting an indication of the determined amount of modulation.

11. The method of claim 10, further comprising:
receiving the indication of the determined amount of modulation at a processor; and
determining with the processor, based on the indication, a status of a power grid comprising the power line.

12. The method of claim 7, wherein:
determining the status comprises detecting a fault or power quality within the power grid.

13. The method of claim 7, wherein:
directing the beam of light through the light modulating member comprises directing the beam through an opening in a conductive layer on a surface of light modulating member.

14. A system comprising:
an underground power line having a plurality of phases and comprising a capacitive test access port;
a plurality of optical voltage sensors, where at least one optical voltage sensor of the plurality of optical voltage sensors is disposed at least partially disposed within the test access port;
where each of the plurality of optical voltage sensors is capacitively coupled to a phase of the plurality of phases; and
the system further comprises a laser and a splitter adapted to direct a portion of a beam from the laser to each of the plurality of optical voltage sensors.

15. The system of claim 14, wherein:
the optical voltage sensor further comprises a conductive, reflective member disposed at the first end; and
the first end is disposed within the test access port with the conductive, reflective member coupled to a conductor of the power line.

16. The system of claim 14, wherein:
the optical voltage sensor further comprises a battery; and
an inductive power pickup configured to couple power from the power line to charge the battery.

17. A system comprising:
an underground power line comprising a capacitive test access port; and
a sensor system at least partially disposed within the test access port, wherein the sensor system measures a phase change in a single beam of light reflected within a light modulating member of the sensor system.

18. The system of claim 17, wherein the sensor system includes a voltage sensor.

19. The system of claim 17, wherein the sensor system includes a current sensor.

20. The system of claim 17, wherein the system includes a processor that processes voltage and current measurements.

21. The system of claim 14, wherein the system includes a current sensor.

22. The system of claim 14, wherein the system includes a processor that processes voltage and current measurements.

23. The system of claim 22, wherein the system includes an automatic data analysis system.

* * * * *